United States Patent
Cheng

(10) Patent No.: US 9,802,892 B2
(45) Date of Patent: Oct. 31, 2017

(54) **METHOD FOR STEPWISE SEPARATING AMINO ACID ACTIVE INGREDIENTS OF *CAMELLIA NITIDISSIMA* CHI**

(71) Applicant: School of Medicine Jiaying University, Meizhou (CN)

(72) Inventor: Jinsheng Cheng, Meizhou (CN)

(73) Assignee: SHENZHEN VIOLIN TECHNOLOGY CO., LTD, Shenzhen (CN)

( * ) Notice: Subject to any disclaimer, the term of this patent is extended or adjusted under 35 U.S.C. 154(b) by 159 days.

(21) Appl. No.: 14/948,249

(22) Filed: Nov. 21, 2015

(65) Prior Publication Data

US 2016/0152564 A1    Jun. 2, 2016

(30) Foreign Application Priority Data

Nov. 26, 2014  (CN) .......................... 2014 1 0688494

(51) Int. Cl.
  *C07C 227/40*  (2006.01)
  *C07D 207/16*  (2006.01)
(52) U.S. Cl.
  CPC .......... *C07D 207/16* (2013.01); *C07C 227/40* (2013.01)
(58) Field of Classification Search
  CPC .................................................. C07C 227/40
  See application file for complete search history.

(56) References Cited

PUBLICATIONS

Roman et al. Eur. Phys. J. D. 2006, 38, 117-120.*

* cited by examiner

*Primary Examiner* — Matthew Coughlin
(74) *Attorney, Agent, or Firm* — Wayne & Ken, LLC; Tony Hom

(57) ABSTRACT

The present invention relates to the technical field of *Camellia nitidissima* Chi processing and application, and provides a method for stepwise separating amino acid active ingredients of *Camellia nitidissima* Chi. The method comprises the following steps: taking a graphene nano material as a selective extraction, adsorption and separation carrier material; carrying out stepwise separation through stepwise controlling the pH value of *Camellia nitidissima* Chi concentrated solution and adjusting the isoelectric points of the amino acid active ingredients, wherein the amino acid active ingredients comprise aspartic acid, threonine, serine, glutamic acid, proline and glycine, and the pH values of the aspartic acid, the threonine, the serine, the glutamic acid, the proline and the glycine corresponding to the stepwise separated isoelectric points are less than 2.77, 5.98-6.15, 3.23-5.67, 2.78-3.21, 6.17-6.29 and 5.69-5.96. The method for stepwise separating amino acid active ingredients of *Camellia nitidissima* Chi has the characteristics of superior selectivity, superior separation speed, good product purity and low cost.

12 Claims, No Drawings

METHOD FOR STEPWISE SEPARATING AMINO ACID ACTIVE INGREDIENTS OF *CAMELLIA NITIDISSIMA* CHI

CROSS-REFERENCE TO RELATED APPLICATIONS

This application is a continuation in part of, and claims priority to, Chinese Patent Application No. 201410688494.7 with a filing date of Nov. 26, 2014. The content of the aforementioned application, including any intervening amendments thereto, is incorporated herein by reference.

TECHNICAL FIELD

The present invention relates to the technical field of *Camellia nitidissima* Chi processing and application, more particularly, to a method for stepwise separating amino acid active ingredients of *Camellia nitidissima* Chi.

BACKGROUND OF THE PRESENT INVENTION

As a national first-class protective plant, *Camellia nitidissima* Chi has good reputation of "Giant Panda of Botany" and "Emperor in Theaceae". The flowers and leaves of *Camellia nitidissima* Chi not only contain rich tea polyphenols, tea polysaccharides, total flavones, β-sitosterol, Se, Mn, Fe, Zn, Ge and other microelements, but also contain rich amino acid active ingredients, such as threonine, serine, glutamic acid, proline, and glycine etc, the content varies slightly with varieties, and the amino acid content of different parts like leaves, flowers, pollen and fruits of *Camellia nitidissima* Chi is also different.

At present, most analysis technologies about amino acid active ingredients of *Camellia nitidissima* Chi are appeared in literatures, and most existing related reports focus on amino acid analysis in *Camellia nitidissima* Chi, few literatures concerned the separation technology, severely restricting the popularization and application of amino acid active ingredients in *Camellia nitidissima* Chi.

SUMMARY OF THE PRESENT INVENTION

To solve the problems in existing technologies, the present invention provides a method for stepwise separating amino acid active ingredients of *Camellia nitidissima* Chi to separate and extract amino acid ingredients in *Camellia nitidissima* Chi. The method has the characteristics of high selectivity, high separation speed, good product purity and low cost.

The content of the present invention is as follows.

A method for stepwise separating amino acid active ingredients of *Camellia nitidissima* Chi, it comprises the following steps, taking a graphene nano material as a selective extraction, adsorption and separation carrier material; carrying out stepwise separation through stepwise controlling the pH value *Camellia nitidissima* Chi concentrated solution and adjusting the isoelectric points of the amino acid active ingredients, wherein the amino acid active ingredients comprise aspartic acid, threonine, serine, glutamic acid, proline and glycine.

Graphene is a new material with single-layered sheet structure composed of carbon atoms. And a flat film of hexagon honeycomb lattice composed of carbon atoms with $sp^2$ hybrid orbital. Besides, graphene is with super-large specific surface, its theoretical specific surface area can up to 2630 $m^2/g$. With excellent properties of super-large specific surface, nano-sized aperture, thickness of atomic layer, surface electrical properties, capable of functional compound modification etc., graphene shows its advantages and potential. forever, graphene materials have unique advantages in biocompatibility and surface charge etc.

As an amphoteric compound, amino acid contains groups capable to release $H^+$ like carboxyl and also contains groups capable to accept $H^+$ like amino, So amino acid is also called ampholyte or zwitterion. When pH=pl (isoelectric points), amino acid is zwitterion and not move in the electric field: when pH>pl, amino acid is negatively charged and move towards positive electrode in electric field; when pH<pl, amino acid is positively charged and move towards negative electrode in electric field. Meanwhile, in *Camellia nitidissima* Chi, wherein the amino acid active ingredients comprise aspartic acid, threonine, serine, glutamic acid, proline and glycine, and the isoelectric points of them are different, so the graphene nano material can be taken as a selective extraction, adsorption and separation carrier material to separate the amino acid active ingredients in *Camellia nitidissima* Chi respectively through adjusting the pH value of *Camellia nitidissima* Chi concentrated solution and adjusting the isoelectric points.

Preferably, the pH values of the aspartic acid, the threonine, the serine, the glutamic acid, the praline and the glycine corresponding to the stepwise separated isoelectric points are less than 2.77, 5.98-6.15, 3.23-5.67, 2.78-3.21, 6.17-6.29 and 5.69-5.96. And the isoelectric points of amino acid need to be separated of the aspartic acid, the threonine, the serine, the glutamic acid, the praline and the glycine are 2.77, 6.16, 5.68, 3.22, 6.30 and 5.97 respectively, the amino acid need to be separated will not interfere with each other by adjusting different pH values, stepwise selective separation can ensure the purity of separation product effectively.

Preferably, there are modified graphene nano materials and unmodified graphene nano materials, wherein the modified graphene nano materials include graphene oxide, hydroxyl graphene, carboxyl graphene, thiol graphene, graphene modified by chitosan, graphene modified by metal ions, graphene modified by polymer or biomacromolecules and graphene-like nanometer mesoporous materials, different types of graphene nano material can be chose as needed to improve separation efficiency.

Preferably, the graphene nano materials are synthesized by renewable resources derived active carbons with improved Hummers method and reversible addition-fragmentation chain transfer polymerization method, and the cost of separating carrier material can be saved effectively.

Preferably, the graphene nano materials can be cleaned, dried, activated to be recycled after the adsorption of corresponding amino acid steps, and the cost of separating carrier material can be saved effectively.

Preferably, raw materials to prepare active carbon by carbonizing renewable resources include straw, bagasse and cornstalk.

Preferably, the processes of stepwise separation also include quicken separation speed by ultrasonic vibration and dispersion, and the separation efficiency can be improved effectively.

Meanwhile, after the completion of amino acid active ingredients stepwise separation of *Camellia nitidissima* Chi concentrated solution, the remained tea polyphenols, tea polysaccharides, total flavones, β-sitosterol, linoleic acid and other *Camellia nittdissima* Chi active ingredients can be separated synchronously after organic solvents are removed by rotary evaporation, the active ingredients of *Camellia*

*nitidissima* Chi can be applied to the fullest, so the manufacturing cost is further reduced.

The advantages of the present invention are as follows.

Firstly, superior selectivity. The isoelectric points of amino acid active ingredients need to be separated are different, stepwise separation can be carried out by adjusting pH values of *Camellia nitidissima* Chi concentrated solution, selective separation can be carried out to the aspartic acid, the threonine, the serine, the glutamic acid, the proline and the glycine, having less interference with each other.

Secondly, superior separation speed. The electronegative characteristic of graphene nano material can be used effectively and the advantage of large specific surface area can be played fully by taking the graphene nano material as selective extraction, adsorption and separation carrier material, and the separation speed can be quickened.

Thirdly, good product purity. Stepwise separation is carried out to the active ingredients of amino acid need to be separated, one amino acid is separated each time, and the isoelectric points of amino acids are different with each other, the non-separated amino acids has less interference with amino acids need to be separated, so the purity of separated amino acids can be ensured.

Fourthly, low cost. There is no need to invest equipment for stepwise separation, as the carrier of extraction, adsorption and separation, graphene carrier material can be recycled, so the separation cost can be saved effectively.

Fifthly, simple operation. Stepwise separation is normal chemical operation, no complicate equipment operation, simple process, so the operational process can be simplified effectively.

DETAILED DESCRIPTION OF PREFERRED EMBODIMENTS

For better understanding of the present invention, the following is detailed description about contents and embodiments of the present invention.

A method for stepwise separating amino acid active ingredients of *Camellia nitidissima* Chi, it comprises the following steps, taking a graphene nano material as a selective extraction, adsorption and separation carrier material; carrying out stepwise separation through stepwise controlling the pH value *Camellia nitidissima* Chi concentrated solution and adjusting the isoelectric points of the amino acid active ingredients, wherein the amino acid active ingredients comprise aspartic acid, threonine, serine, glutamic acid, proline and glycine. The method comprise following steps:

Step 1: preparation of *Camellia nitidissima* Chi concentrated solution: fresh flowers of *Camellia nitidissima* Chi in autumn were picked and weighted with electronic scale; the picked flowers were chose for the freshest and excellent quality flowers and those with poor quality are removed, the optimized flowers must comply with requirements of *Pharmacopoeia of China* (2010), that is, no mildew, no odor and no impurity, the optimized flowers of *Camellia nitidissima* were smashed by grinder after cleaning; some acetone or ethanol with over 95% concentration was added into smashed leaves of *Camellia nitidissima* Chi and was extracted for 5-6 h by Soxhlet extractor to obtain the first concentrated solution; then some acetone or ethanol with over 95% concentration was added into extracted residue and ultrasound was performed for 1.5 h under 40-60° C. to obtain the second concentrated solution; the first and second concentrated solution was mixed, and acetone or ethanol solvent was removed by rotary evaporation of rotary evaporators, finally the *Camellia nitidissima* Chi concentrated solution A1 in organic phase was obtained.

Step 2: stepwise separation of proline, comprising following steps:

At first, carrying out pH adjustment, the pH value of *Camellia nitidissima* Chi concentrated solution obtained in step 1 was adjusted to 6.17-6.29, by this time, the pH value of *Camellia nitidissima* Chi concentrated solution was less than isoelectric point of the proline only, but more than any other isoelectric points of amino acids, and because when pH>pI, the amino acid was negatively charged, when pH<pI, the amino acid was positively charged, by this time, the proline was positively charged, while the aspartic acid, the threonine, the serine, the glutamic acid, and the glycine were all negatively charged.

Next, carrying out proline selective extraction, some graphene nano materials were added into the *Camellia nitidissima* Chi concentrated solution A1 after pH adjustment and ultrasound was performed for half an hour, the positively charged proline was combined with the negatively charged graphene nano material assisted by ultrasonic wave, and graphene oxide was taken as the graphene nano material, other negatively charged amino acids were not combined with the graphene nano material, then the *Camellia nitidissima* Chi concentrated solution B1 was obtained.

Then carrying out proline stepwise separation, the suction filtration is carried out to the *Camellia nitidissima* Chi concentrated solution B1 after ultrasound to obtain the first filtrate C1 and the first filter residue D1, and the first filter residue D1 was washed with acetone for several times to remove some simple adsorbed non-proline ingredients, while the first filtrate C1 was left to be used for next step, the collected first filter residue D1 was placed into the beaker with 95% ethanol, and ultrasound was performed for an hour, then the second filtrate E1 and the second filter residue F1 were obtained through filtration, the second filter residue F1 was washed with ethanol for several times, after drying and activating, it was left to be subsequent recycled, the ethanol of the second filtrate E1 was removed by rotary evaporation, after drying, the proline product with white crystalline powder can be obtained, besides, the proline product can be further purified through recystallization.

Step 3: stepwise separation of threonine, comprising following steps:

At first, carrying out pH adjustment, the pH value of the first filtrate C1 obtained in step 2 was adjusted to 5.98-6.15 according to the pH adjustment method of step 2, by this time, the threonine was positively charged, while other amino acids were negatively charged;

Next, carrying out threonine selective extraction, some graphene nano materials were added into the first filtrate C1 and ultrasound was performed for half an hour, the positively charged threonine was combined with the negatively charged graphene nano material assisted by ultrasonic wave, and hydroxyl graphene was taken as the graphene nano material, other negatively charged amino acids were not combined with the graphene nano material, then the *Camellia nitidissima* Chi concentrated solution B2 was obtained.

Then carrying out threonine stepwise separation, the suction filtration was carried out to the *Camellia nitidissima* Chi concentrated solution B2 to obtain the first filtrate C2 and the first filter residue D2, and the first filter residue D2 was washed with acetone for several times to remove some simple adsorbed non-threonine ingredients, while the first filtrate C2 was left to be used for the second extraction, the collected first filter residue D2 was placed into the beaker with hot water, and ultrasound was performed for half an hour, then the second filtrate E2 and the second filter residue F2 were obtained through immediate filtration, the second filter residue F2 was washed with hot water for several times, after drying and activating, it was left to be subsequent recycled, the second filtrate E2 was placed into the beaker and heated to high temperature, in a successive step, the beaker with the second filtrate E2 was placed into ice water mixture immediately, the threonine product can be obtained after the precipitated white crystal was separated and dried, besides, the product can be further purified through recystallization.

Step 4: stepwise separation of glycine, comprising following steps:

At first, carrying out pH adjustment, the pH value of the first filtrate C2 obtained in step 3 was adjusted to 5.69-5.96 by repeating the pH adjustment, by this time, the glycine was positively charged, while other amino acids were negatively charged;

Next, carrying out glycine selective extraction, some graphene nano materials were added into the second filtrate C2 and the mixed materials of hydroxyl graphene and thiol graphene were taken as the graphene nano material, ultrasound was performed for half an hour, and the positively charged glycine was combined with the negatively charged graphene nano material assisted by ultrasonic wave, then the *Camellia nitidissima* Chi concentrated solution B3 to be separated was formed.

Then carrying out glycine stepwise separation, the suction filtration was carried out to the *Camellia nitidissima* Chi concentrated solution B3 to obtain the first filtrate C3 and the first filter residue D3, and the first filter residue D3 was washed with acetone for several times to remove some simple adsorbed non-glycine ingredients, while the first filtrate C3 was left to be used for the second extraction, the collected first filter residue D3 was placed into the beaker with deionized water, and ultrasound was performed for half an hour, then the second filtrate E3 and the second filter residue F3 were obtained through filtration, the second filter residue F3 was washed with hot water for several times, after drying and activating, it was left to be subsequent recycled, the second filtrate was decompressed to remove water, and the white crystal powder can be obtained, the glycine product can be obtained after the obtained white crystal powder was separated and dried, besides, the product can be further purified through recystallization.

Step 5: stepwise separation of serine, comprising following steps:

At first, carrying out pH adjustment, the pH value of the first filtrate C3 obtained in step 4 was adjusted to 3.23- 5.67 by repeating the pH adjustment, by this time, the serine was positively charged, while other amino acids were negatively charged;

Next, carrying out serine selective extraction, some graphene nano materials were added into the second filtrate C3 and ultrasound was performed for half an hour, the positively charged serine was combined with the negatively charged graphene nano material assisted by ultrasonic wave, then the *Camellia nitidissima* Chi concentrated solution. B4 to be separated was formed.

Then carrying out serine stepwise separation, the suction filtration as carried out to the *Camellia nitidissima* Chi concentrated solution B4 to obtain the first filtrate C4 and the first filter residue D4 and the first filter residue D4 was washed with acetone for several times to remove some simple adsorbed non-serine ingredients, while the first filtrate C4 was left to be used for the second extraction, the collected first filter residue D4 was placed into the beaker with 95% methanol, and ultrasound was performed for half an hour, then the second filtrate E4 and the second filter residue F4 were obtained through filtration, the second filter residue F4 was washed with methanol for several times, after drying and activating, it was left to be subsequent recycled, the methanol of the second filtrate E4 was removed by rotary evaporation, and the white crystal can be obtained, the serine product can be obtained after the obtained white crystal was separated and dried, the product can be further purified through recystallization.

Step 6: stepwise separation of glutamic acid, comprising allowing steps:

At first, carrying out pH adjustment, the pH value of the first filtrate C4 obtained in step 5 was adjusted to 2.78- 3.21 by repeating the pH adjustment, by this time, the glutamic acid was positively charged, while other amino acids were negatively charged;

Next, carrying out glutamic acid selective extraction, some graphene nano materials were added into the second filtrate C4 and the mixed materials of unmodified graphene, graphene modified by chitosan and graphene modified by metal ions were taken as the graphene nano material, ultrasound was performed for half an hour, and the positively charged glutamic acid was combined with the negatively charged graphene nano material assisted by ultrasonic wave, then the *Camellia nitidissima* Chi concentrated solution. B5 to be separated was formed.

Then carrying out glutamic acid stepwise separation, the suction filtration was carried out to the *Camellia nitidissima* Chi concentrated solution B5 to obtain the first filtrate C5 and the first filter residue D5, and the first filter residue D5 was washed with acetone for several times to remove some simple adsorbed non-glutamic acid ingredients, and the first filtrate C5 was left to be used for the second extraction, while the first filter residue D5 was placed into the beaker with hot water after collection, and performing ultrasound for half an hour, then the second filtrate E5 and the second filter residue F5 were obtained through immediate filtration, the second filter residue was washed with hot water for several times, after drying and activating, it was left to be subsequent recycled, the second filtrate was placed into the beaker and heated to high temperature, in a successive step, the beaker with the second filtrate E5 was placed into ice water mixture immediately, the threonine product can be obtained after the precipitated scaly crystal was separated and dried, besides, the product can be further purified through recystallization.

Step 7: stepwise separation of aspartic acid, comprising following steps:

At first, carrying out pH adjustment, the pH value of the first filtrate C5 obtained in step 6 was adjusted to be less than 2.77 by repeating the pH adjustment, by this time, the aspartic acid was positively charged.

Next, carrying out aspartic acid selective extraction, some graphene nano materials were added into the first filtrate C5 and the mixed materials of graphene modified by biomacromolecule and graphene-like nanometer mesoporous material were taken as the graphene nano material, ultrasound was performed for half an hour, and the positively charged aspartic acid was combined with the negatively charged graphene nano material assisted by ultrasonic wave, then the *Camellia nitidissima* Chi concentrated solution B6 to be separated was obtained.

Then carrying out aspartic acid stepwise separation, the suction filtration was carried out to the *Camellia nitidissima* Chi concentrated solution 86 to obtain the first filtrate C6 and the first filter residue D6, and the first filter residue D6 was washed with acetone for several times to remove some simple adsorbed non-aspartic acid ingredients, while the first filtrate C6 was left to be used for the extraction of other ingredients, the collected first filter residue D6 was placed into the beaker with hot water, and ultrasound was performed for half an hour, then the second filtrate E6 and the second residue F6 were obtained through immediate filtration, the second filter residue was washed with hot water for several times, after drying and activating, it was left to be subsequent recycled, the second filtrate was placed into the beaker and heated to high temperature, in a successive step, the beaker with the second filtrate E6 was placed into ice water mixture immediately, the threonine product can be obtained after the precipitated scaly crystal was separated and dried, besides, the product can be further purified through recystallization.

The first filtrate E6 after removing the amino acid active ingredients contains rich active ingredients, such as tea polyphenols, linoleic acids, total flavones, tea polysaccharides, they can be used for the development of other products of Camellia nitidissima Chi through comprehensive utilization.

To reduce the cost effectively, the graphene nano materials are synthesized by renewable resources derived active carbons with improved Hummers method and reversible addition-fragmentation chain transfer polymerization method. The raw materials to prepare active carbon by carbonizing renewable resources include straw, bagasse and cornstalk.

The above disclosure merely shows several specific embodiments of the present invention, and the present invention is not limited thereto; those ordinary skilled in the art complete the implementation of the present invention without difficulty based on the description and above disclosure; while it should be noted to those skilled in the art that several variations, modification and improvements can also be made within the scope of technical proposal, and these variations, modification and improvements are equivalent embodiments; moreover, they are also considered within the protective scope of the present invention.

I claim:

1. A method for stepwise separating amino acid active ingredients of Camellia nitidissima Chi, characterized in that it comprises the following steps:
   utilizing a graphene nano material as a selective extraction, adsorption and separation carrier material;
   carrying out stepwise separation through stepwise controlling the pH value of a Camellia nitidissima Chi concentrated solution; and
   adjusting the isoelectric points of the amino acid active ingredients;
   wherein the amino acid active ingredients comprise aspartic acid, threonine, serine, glutamic acid, proline and glycine.

2. The method for stepwise separating amino acid active ingredients of Camellia nitidissima Chi according to claim 1, characterized in that the pH values of the aspartic acid, the threonine, the serine, the glutamic acid, the proline and the glycine corresponding to the stepwise separated isoelectric points are less than 2.77, 5.96-6, 15, 3.23-5.67, 2.78-3.21, 6.17-6.29 and 5.69-5.96, respectively.

3. The method for stepwise separating amino acid active ingredients of Camellia nitidissima Chi according to claim 1, characterized in that the graphene nano materials are selected from graphene oxide, hydroxyl graphene, carboxyl graphene, thiol graphene, graphene modified by chitosan, graphene modified by metal ions, and graphene modified by polymer or biomacromolecules.

4. The method for stepwise separating amino acid active ingredients of Camellia nitidissima Chi according to claim 3, characterized in that the graphene nano materials are synthesized by renewable resources derived active carbons with an improved Hummers method or reversible addition-fragmentation chain transfer polymerization method.

5. The method for stepwise separating amino acid active ingredients of Camellia nitidissima Chi according to claim 4, characterized in that the graphene nano materials are cleaned, dried, activated to be recycled after the adsorption of corresponding amino acid steps.

6. The method for stepwise separating amino acid active ingredients of Camellia nitidissima Chi according to claim 5, characterized in that raw materials to prepare active carbon by carbonizing renewable resources are selected from straw, bagasse and cornstalk.

7. The method for stepwise separating amino acid active ingredients of Camellia nitidissima Chi according to claim 6, characterized in that the processes of stepwise separation also include increasing separation speed by ultrasonic vibration and dispersion.

8. The method for stepwise separating amino acid active ingredients of Camellia nitidissima Chi according to claim 2, characterized in that the graphene nano materials are selected from graphene oxide, hydroxyl graphene, carboxyl graphene, thiol graphene, graphene modified by chitosan, graphene modified by metal ions, and graphene modified by polymer or biomacromolecules.

9. The method for stepwise separating amino acid active ingredients of Camellia nitidissima Chi according to claim 8, characterized in that the graphene nano materials are synthesized by renewable resources derived active carbons with an improved Hummers method or reversible addition-fragmentation chain transfer polymerization method.

10. The method for stepwise separating amino acid active ingredients of Camellia nitidissima Chi according to claim 9, characterized in that the graphene nano materials are cleaned, dried, activated to be recycled after the adsorption of corresponding amino acid steps.

11. The method for stepwise separating amino acid active ingredients of Camellia nitidissima Chi according to claim 10, characterized in that raw materials to prepare active carbon by carbonizing renewable resources are selected from straw, bagasse and cornstalk.

12. The method for stepwise separating amino acid active ingredients of Camellia nitidissima Chi according to claim 11, characterized in that the processes of stepwise separation also include increasing separation speed by ultrasonic vibration and dispersion.

* * * * *